(12) United States Patent
Müller (10) Patent No.: US 6,551,324 B2
(45) Date of Patent: Apr. 22, 2003

(54) INSTRUMENTATION FOR THE PRODUCTION OF FIXING SURFACES FOR A KNEE JOINT ENDOPROSTHESIS

(75) Inventor: Peter Müller, Dachsbach (DE)

(73) Assignee: Peter Brehm, Weisendorf (DE)

(*) Notice: Subject to any disclaimer, the term of this patent is extended or adjusted under 35 U.S.C. 154(b) by 0 days.

(21) Appl. No.: 09/793,898

(22) Filed: Feb. 28, 2001

(65) Prior Publication Data

US 2001/0018589 A1 Aug. 30, 2001

(30) Foreign Application Priority Data

Feb. 29, 2000 (DE) .......................................... 100 09 697

(51) Int. Cl.⁷ .............................................. A61B 17/56
(52) U.S. Cl. ............................................ 606/88; 606/80
(58) Field of Search .................. 606/79, 80, 82, 606/86–89, 96, 179, 180; 433/223, 75, 76; 408/103–109

(56) References Cited

U.S. PATENT DOCUMENTS

| 4,777,942 A | | 10/1988 | Frey et al. |
| 4,896,663 A | * | 1/1990 | Vandewalls .................. 606/79 |
| 5,228,459 A | | 7/1993 | Caspari et al. |
| 5,281,136 A | * | 1/1994 | Gianella et al. .............. 433/76 |
| 5,468,243 A | * | 11/1995 | Halpern ....................... 606/80 |
| 5,649,928 A | | 7/1997 | Grundei |
| 5,776,136 A | * | 7/1998 | Sahay et al. .................. 606/79 |
| 5,782,636 A | * | 7/1998 | Armstrong et al. ......... 433/165 |

FOREIGN PATENT DOCUMENTS

| DE | 93 01 611 | 7/1993 |
| DE | 297 09 287 | 11/1998 |
| DE | 297 20 105 | 4/1999 |
| EP | 0 315 338 | 5/1989 |
| EP | 0 376 657 | 7/1990 |
| EP | 0 720 834 | 7/1996 |
| FR | 2 664 157 | 1/1992 |
| FR | 2 721 202 | 12/1995 |
| FR | 2 726 178 | 5/1996 |

* cited by examiner

Primary Examiner—Eduardo C. Robert
Assistant Examiner—Michael B. Priddy
(74) Attorney, Agent, or Firm—Browdy and Neimark, P.L.L.C.

(57) ABSTRACT

In an instrumentation for the production of fixing surfaces for fixing a knee joint endoprosthesis to the femoral condyle that is adjacent to the knee, and to the tibial head, provision is made for a rotary milling head, which is fixable in relation to the longitudinal axis of the femur and tibia, respectively, by fastening means and which, in relation to this longitudinal axis, is angularly adjustable in a stable stop position by being pivoted, defining milling planes, and which is displaceable in the set milling plane, covering same and working as a face milling cutter or as a cylindrical milling cutter.

20 Claims, 9 Drawing Sheets

INSTRUMENTATION FOR THE PRODUCTION OF FIXING SURFACES FOR A KNEE JOINT ENDOPROSTHESIS

BACKGROUND OF THE INVENTION

1. Field of the Invention

The invention relates to an instrumentation for the production of fixing surfaces for a knee joint endoprosthesis on the femoral condyle that is adjacent to the knee joint and on the tibial head.

2. Background Art

A knee joint prosthesis of the type under regard is described for instance in DE 41 02 509 C2, FIG. 3 of which illustrates in particular the fixing surfaces needed for implantation of the part of the prosthesis on the femoral side, i.e. for fixing to the end of the thigh on the side of the knee. This plurality of fixing surfaces which are disposed at an angle to each other is conventionally produced by a rod, which extends in the axial direction of the bone, being inserted in the medullary space after exposure of the bones; by the aid of a saw template which is fixed to the rod and directly to the bone, the individual planes are sawed successively by means of a saw.

Positioning the templates non-displaceably during sawing requires extensive implementation, however really perfect and non-displaceable positioning will not be attained successfully. Moreover, the necessary processes are complicated, leading to comparatively high inaccuracy and unnecessarily long operation times, which places strain on the patient and ultimately also on the operating surgeon. The conventional preparation of these fixing surfaces is specified in detail for example in the leaflet entitled "MC-KNIEGELENK nach Prof. Dr. Diehl", page 5 f.

SUMMARY OF THE INVENTION

It is an object of the invention to embody an instrumentation which will ensure a simple, rapid and accurate way of preparing the fixing surfaces needed for implantation of the tibial part and in particular the femoral part of a prosthesis.

According to the invention, this object is attained by a rotary milling head which is fixable in relation to the longitudinal axis of the femur and tibia, respectively, by fasteing means and which, in relation to this longitudinal axis, is angularly adjustable in a stable stop position by being pivoted, defining milling planes, and which is displaceable in the set milling plane, covering same and working as a face milling cutter or as a cylindrical milling cutter.

As a result of the design according to the invention, the fundamental problems of conventional sawing by the aid of a template no longer occur. Moreover, after treatment and fine machining (subsequent adjustment) are possible, should this be necessary or desirable.

By advantage, the fastening means comprise clamps which enclasp the respective bone.

In this case, a first clamp may grip the bone from above, the clamp having two jaws which are displaceable one in relation to the other and fixable in a stop position.

The fastening means may comprise at least a second clamp, the legs of which are approximately parallel to the longitudinal axis of the bone and displaceable one in relation to the other, with fastening thorns and/or holes into which to insert fastening screws being formed on the ends of the legs.

The thorns provided according to the invention ensure preliminary adjustment for holes to be drilled in the bone for the fastening screws or during the screwing process. The milling equipment can be detached from the fixing component at any time and later on it can be fastened again precisely in its initial position by quick-acting closures.

Preferably the milling head is designed for adjustment in height so that corresponding setting is possible for a certain fixing surface to be formed. Height adjustment may advantageously be put into practice by a threaded spindle of a stable or stabilizable stop position.

In keeping with a preferred embodiment it is provided that, with the milling angle set, the milling head is linearly translationally displayable via guide bars and movable via a pivot bearing or cross support so that a milling plane is defined in this way which can be worked successively by the milling head. The milling head has a cylindrical configuration with the surface of the cylinder forming the milling surface and the front of the cylinder running preferably parallel to the milling plane.

By advantage, further provision is made for an equipment for presetting the position of the axis of the leg, it being possible in this way to consider whether the patient has a varus-valgus deformity. Also leg rotation (varus or valgus deformity) can be corrected and adjusted accurately.

Furthermore, provision is made for equipments setting the length of a leg and the size of the prosthesis.

In the scope of the invention, it is possible to move the milling head or milling cutter manually, using the guide according to the invention.

By alterative, actuation in particular by servo motor can be provided for the setting equipments and/or the motion of the milling head in the milling plane, triggering of the servo motors being advantageously computer controlled. Correspondingly, it is possible to make the whole operation computer-controlled, in particular also in dependence on X-ray or computer tomography images.

For navigation purposes and in replacement of manual handling and setting of the milling head, the instrumentation may be equipped with infrared markers in order for computer-controlled setting to be possible, combined with a three dimensional computer animation on the display screen which has been obtained by a preceding computer tomography.

Details of the invention will become apparent from the ensuing description of a preferred embodiment taken in conjunction with the drawing.

DESCRIPTION OF THE PREFERRED EMBODIMENT

The drawing illustrates a milling cutter 1 with a milling head 2 which is driven in rotation and may function as a cylindrical milling cutter with its surface area 3 being used as well as a face milling cutter with its frontal surface 4 being used. When the cutting planes I to III are prepared—as described below—the milling head 2 is employed as a face milling cutter, whereas it is employed as a cylindrical milling cutter for the preparation of the cutting planes IV and V.

Figure 1:
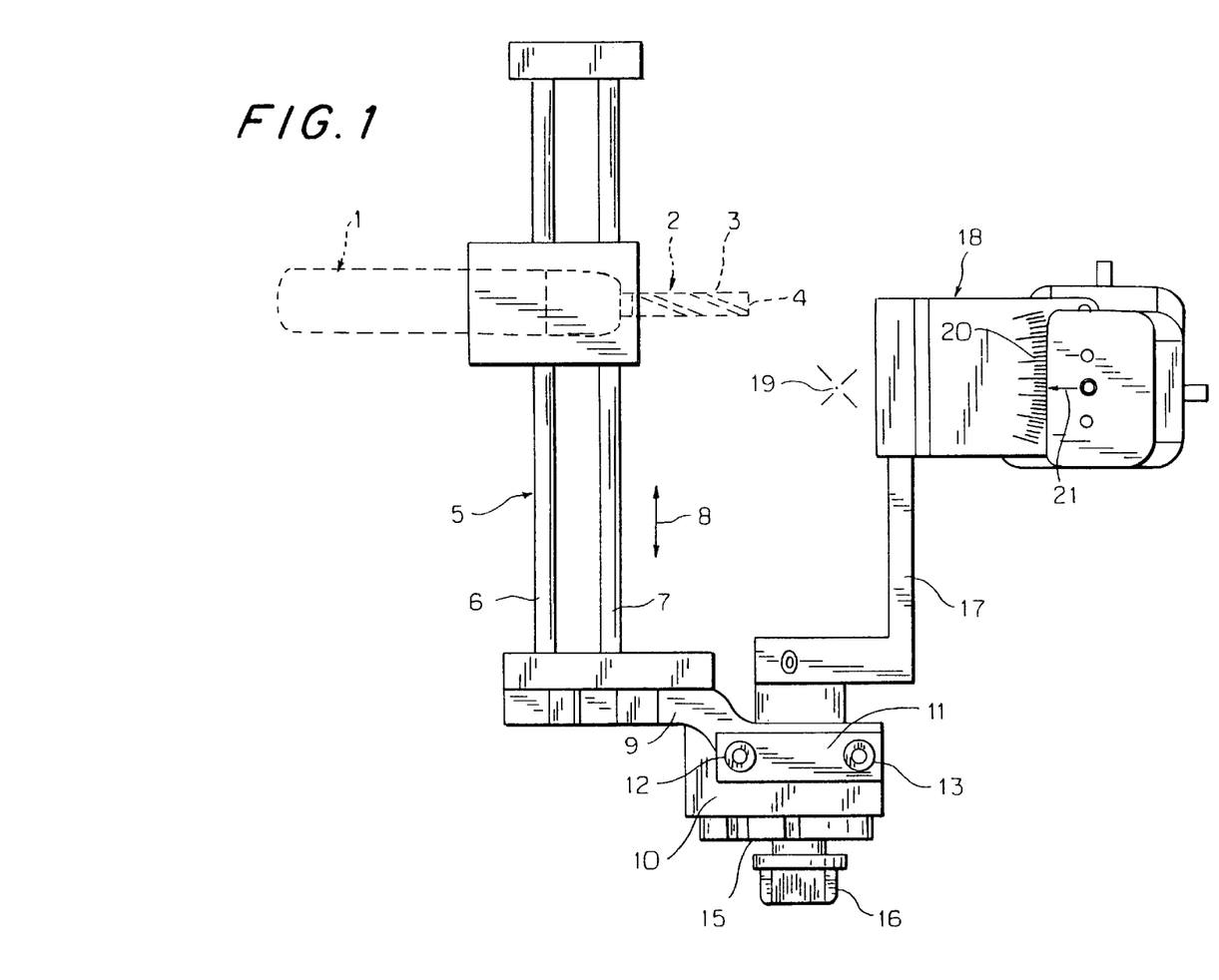
FIG. 1 is a plan view of the instrumentation according to the invention with the milling cutter being positioned horizontally.

The milling cutter 1 is lengthwise displaceable in the direction of the double-headed arrow 8 of FIG. 1 on an x-guide 5 which comprises two parallel bars 6, 7.

Figure 2:
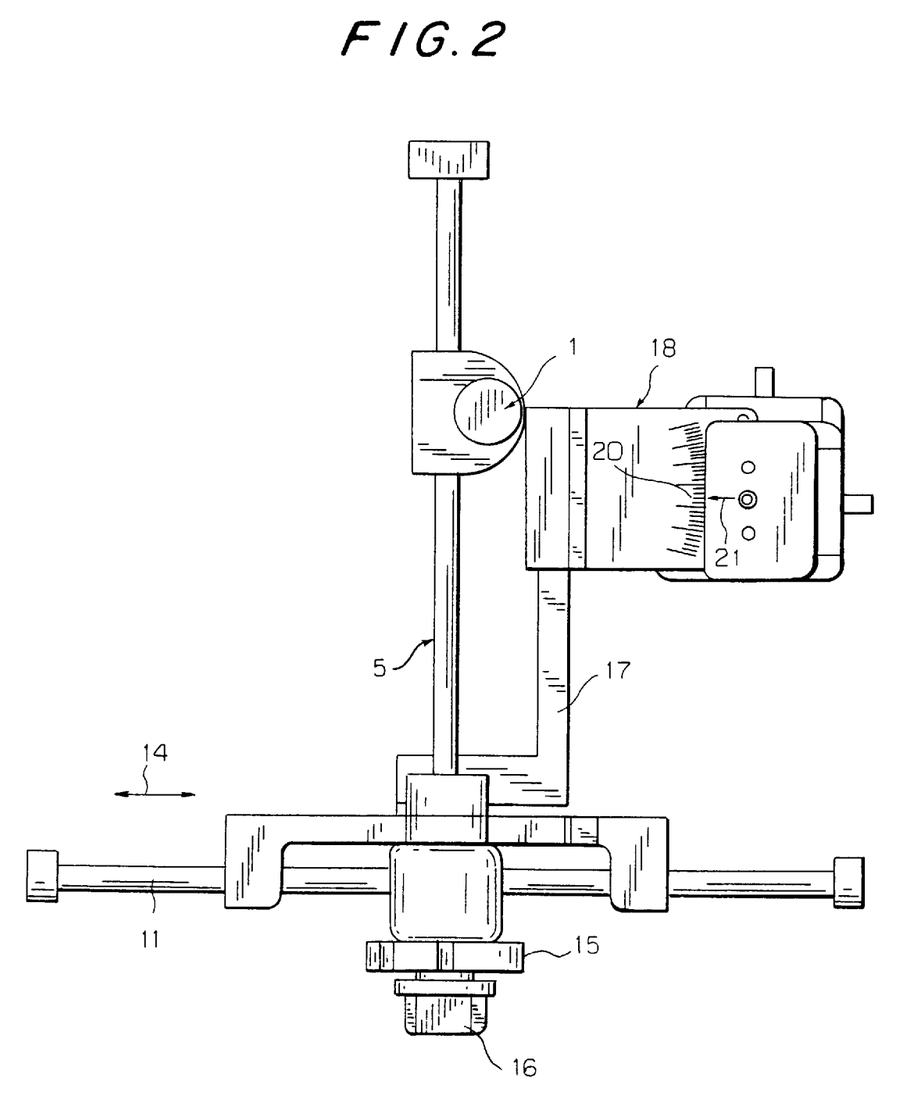
FIG. 2 is an illustration, corresponding to FIG. 1, with the milling cutter being positioned vertically.

By means of a mounting 9, the x-guide 5 is fastened on a bearing block 10, from which a y-guide 11 extends in a direction vertical of the x-guide 5; the y-guide 11 also comprises two bars 12, 13, enabling the milling cutter 1 to be displaced for up and down adjustment in the direction of the double-headed arrow 14 in FIG. 2.

The bearing block 10 is further equipped with a disk can 15 which ensures various pivoting angles to be set in stable stop positions corresponding to the cutting planes I to V; the stop positions are fixable by a locking screw 16.

A setting block 18 is joined to the bearing block 10 via an arm 17, this setting block 18 ensuring a pivoting motion about a pivot axis 19 which is positioned outside the setting block 18; a scale 20 cooperates with a stationary marking 21 for corrective setting in the case of lateral concavity or convexity of the leg (varus-valgus correction). The advantage of this corrective arrangement resides in that any setting or adjustment will not affect the other axes.

Figure 3:
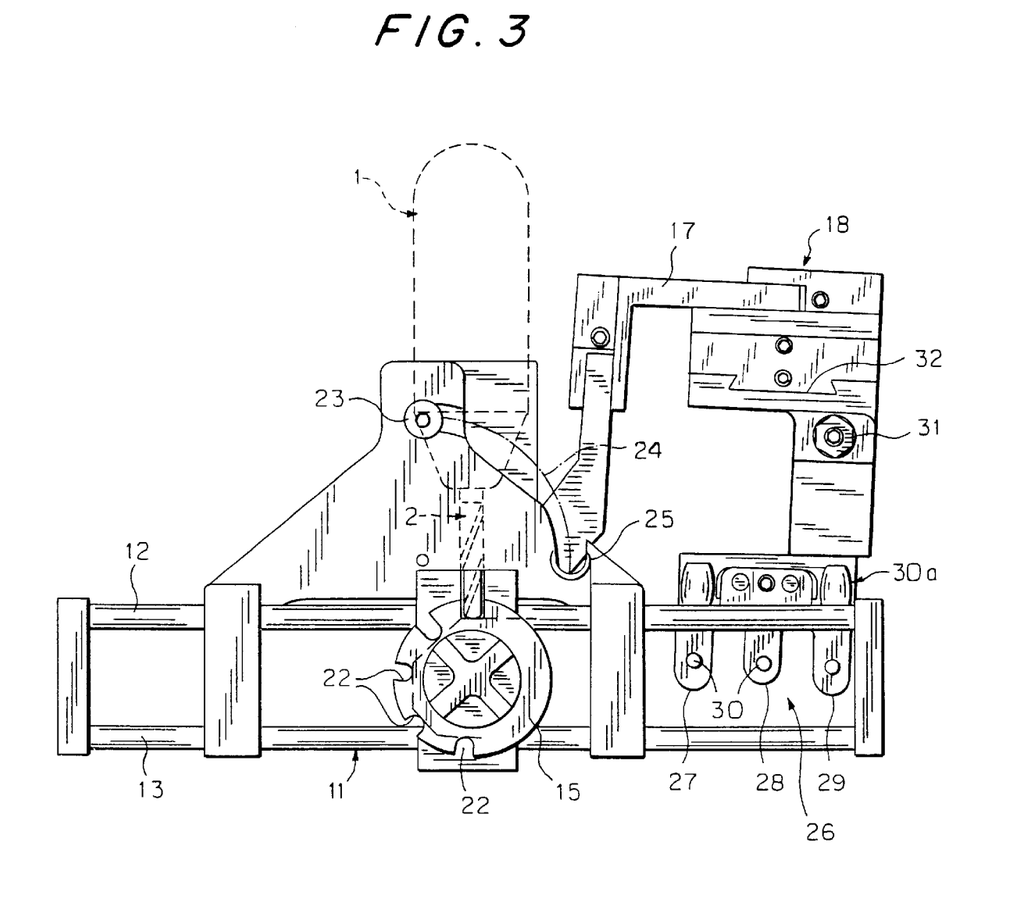
FIG. 3 is a side view with the milling cutter being positioned perpendicularly in the cutting plane I.

FIG. 3 illustrates recesses 22 in the disk can 15 which serve for setting the milling planes I to V. FIG. 3 further shows a detent 23 enabling the milling cutter 1 to be used as a face milling cutter, the milling cutter 1 is pivotal along the curvature 24 by 90°, arresting in the detent 25 where it works as a cylindrical milling cutter.

FIG. 3 further illustrates a bone clamp 26 which comprises three joined-on clamp pieces 27, 28, 29 each with a thorn 30 standing out; this bone clamp 26 is easily detachable by way of a quick-acting closure 30a.

FIG. 3 further clearly shows a setscrew 31 for anterior-posterior setting as well as a dovetail guide 32 for medial-lateral setting.

Figure 4:
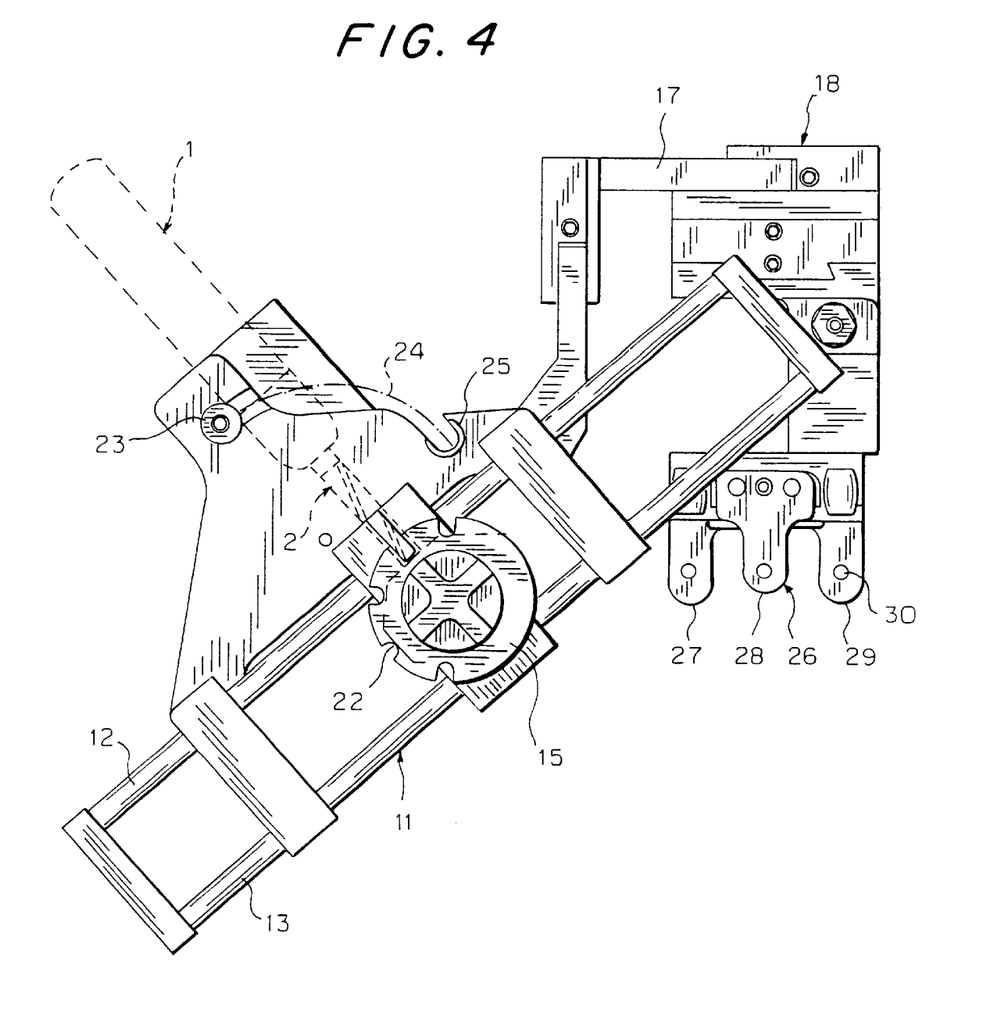
FIG. 4 is a side view, corresponding to FIG. 3, with the milling cutter being positioned perpendicularly in the cutting plane II.

FIG. 4 is a view corresponding to FIG. 3 in which the milling cutter 1 is positioned perpendicularly on the cutting plane II, preparing same by way of face milling.

Figure 5:
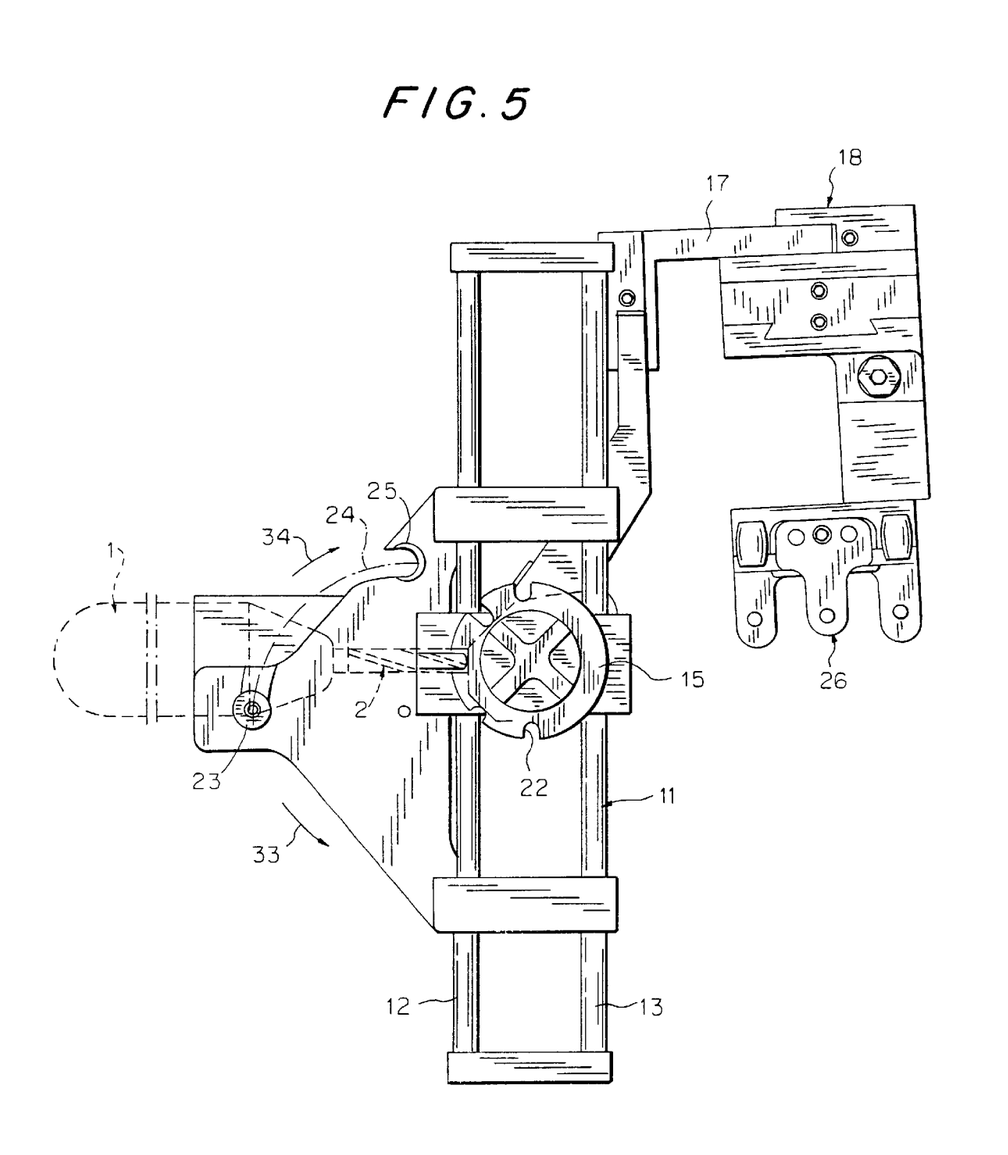
FIG. 5 is a corresponding side view with the milling cutter being positioned perpendicularly in the cutting plane III.

In the position seen as a side view in FIG. 5, preparing the cutting plane III takes place by way of face milling, i.e. the milling cutter 1 is positioned perpendicularly in the cutting plane III.

The arrow 33 illustrates that the milling cutter 1 which works as a femoral cutter can be employed as a tibial cutter by being pivoted in the direction of the arrow 33.

Figure 6:
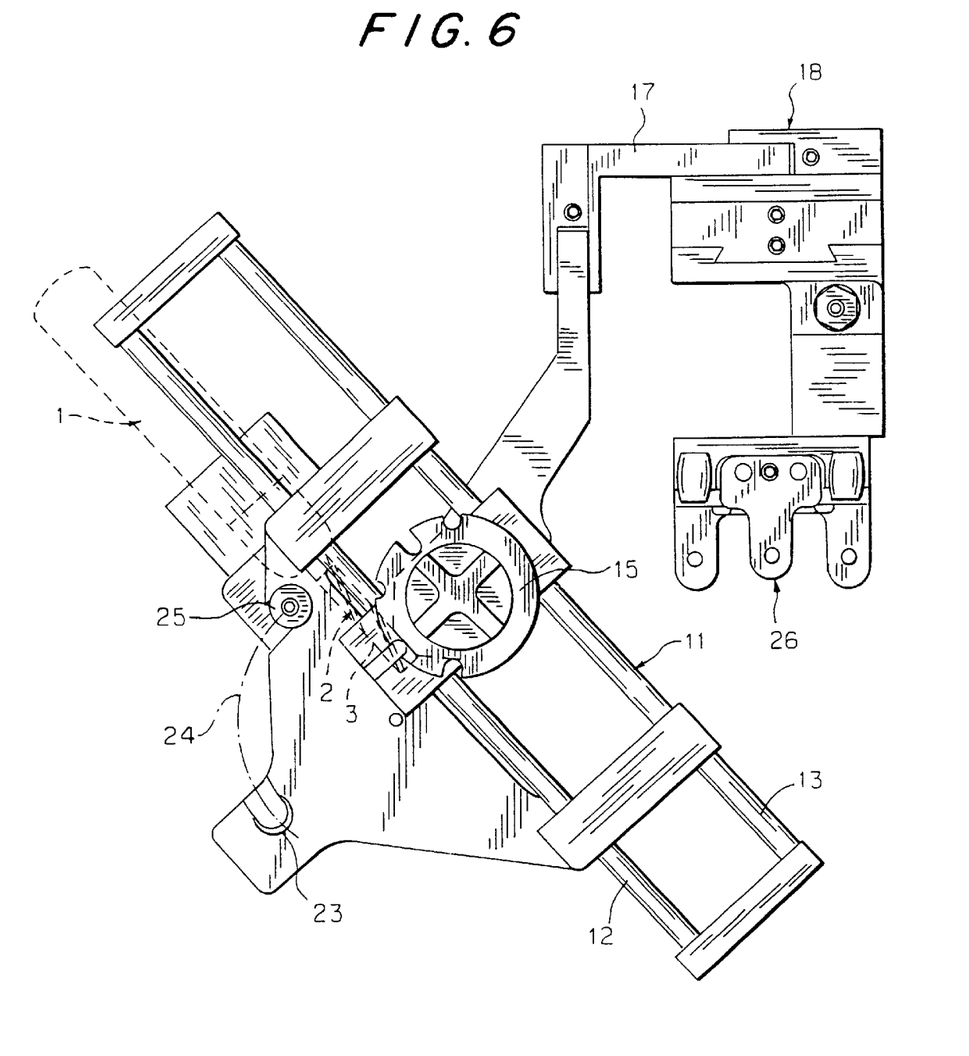
FIG. 6 is a corresponding side view with the milling cutter being positioned in parallel to the cutting plane IV.

Proceeding from the position seen in FIG. 5, pivoting the milling cutter 1 or the milling head 2 takes place along the curvature 24 in the direction of the arrow 34 into the position seen in FIG. 6 where the milling cutter 1 is used as a cylindrical milling cutter with its surface area 3 being employed for the preparation of the cutting plane V by the milling cutter 1 running parallel to this cutting plane V.

Figure 7:
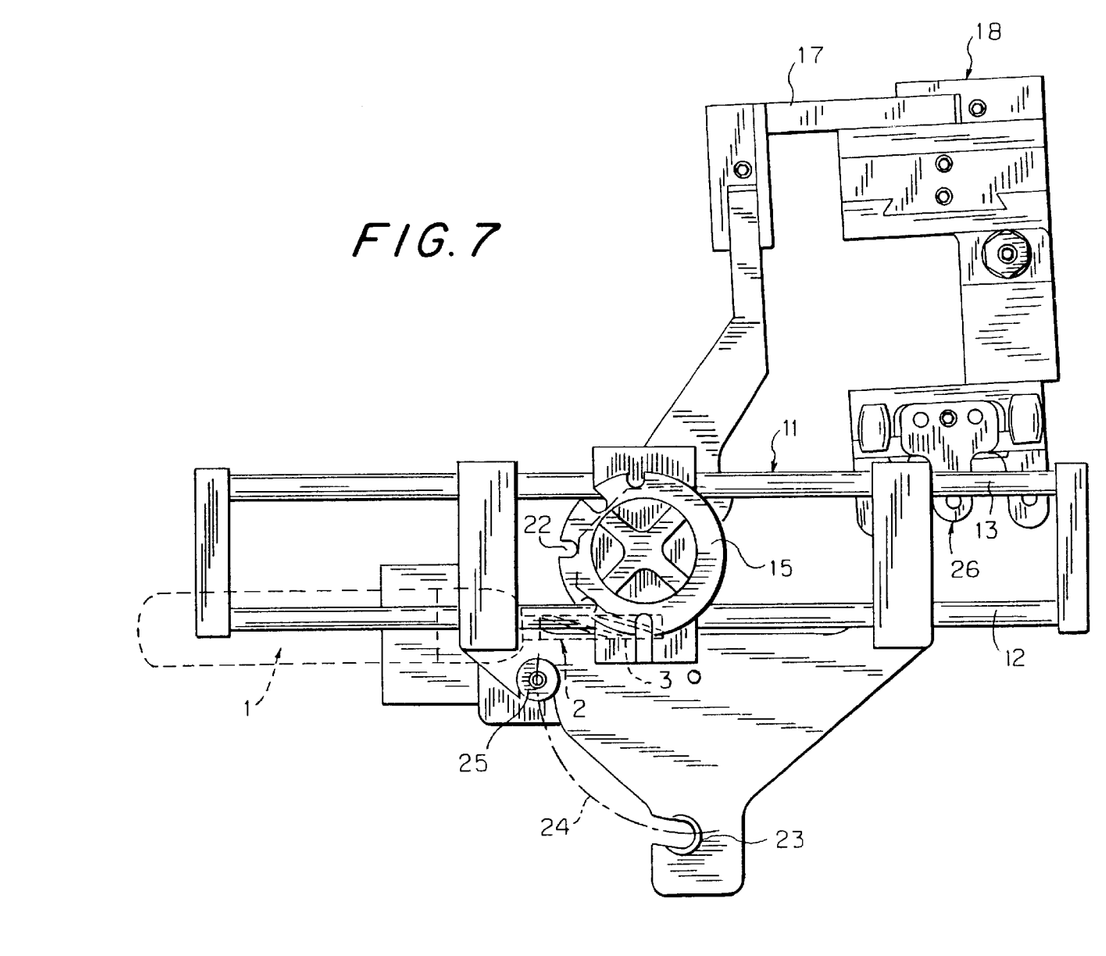
FIG. 7 is a side view with the milling cutter being positioned in parallel to the cutting plane V.

When set as seen in FIG. 7, the milling cutter 1 equally works as a cylindrical milling cutter by being displaced parallel to the cutting plane, producing same.

Figure 8:
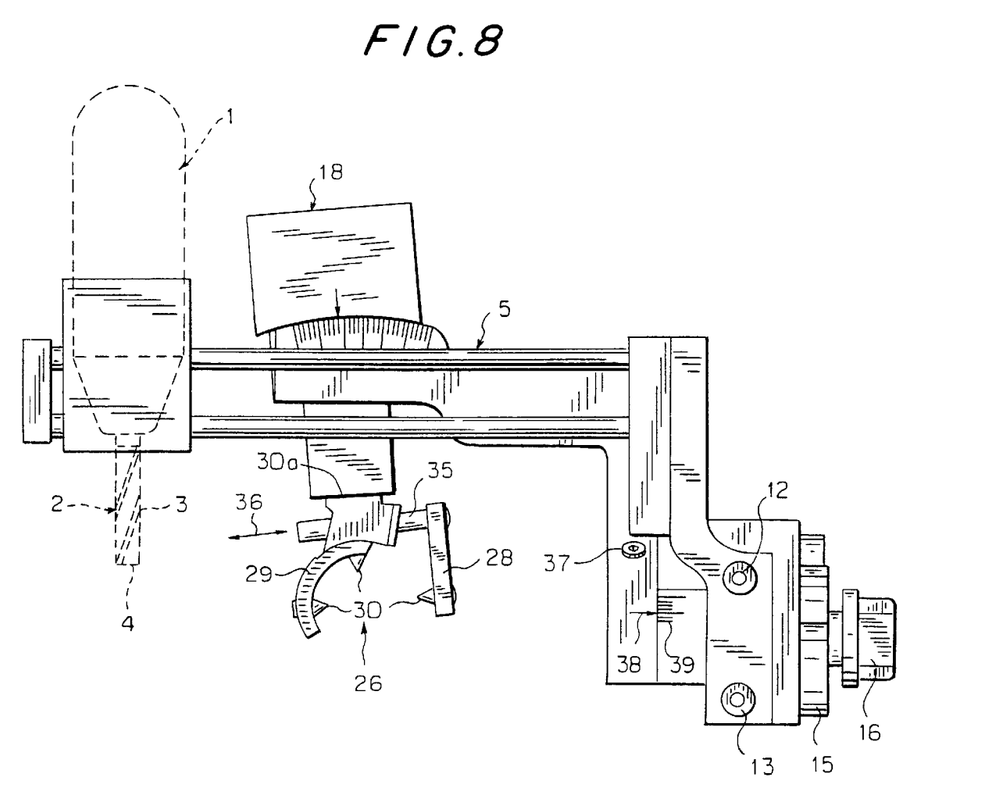
FIG. 8 is a front view with the milling cutter being positioned verticaly.

FIG. 8 is an elevation with the milling cutter 1 positioned vertically. Again the bone clamp 26 is visible, the central joined-on clamp piece 28 being adjustable by way of a guide 35 in the direction of the double-headed arrow 36 for the bone to be fixed or released.

FIG. 8 illustrates a setscrew 37 which acts on a self-locking worm gear for setting the inclination in cooperation with a stationary marking 38 and a pivotal scale 39.

Figure 9A:
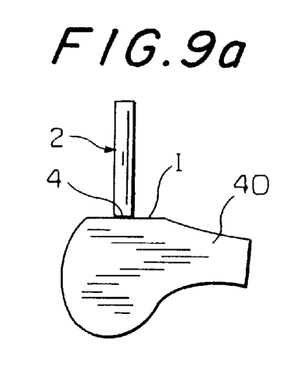
FIGS. 9a to 9f are illustrations of a femoral bone and the position of the milling cutter relative to the femoral bone as well as the cutting planes I to V produced on the femoral bone by means of the milling cutter.

The following is another explication of the mode of operation of the instrumentation according to the invention, taken in conjunction with FIG. 9;

As seen in FIG. 9a, the first cutting plane I is prepared by way of face milling, the frontal face 4 of the milling head 2 being positioned vertically in the cutting plane I. In this case, the instrumentation has the setting seen in FIG. 2.

Figure 9B:
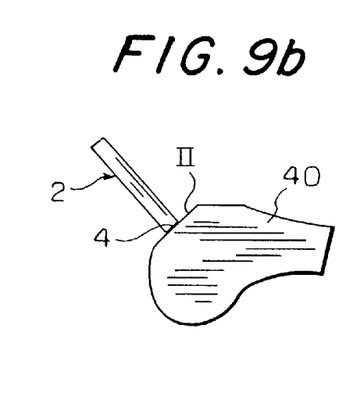
Figure 9C:
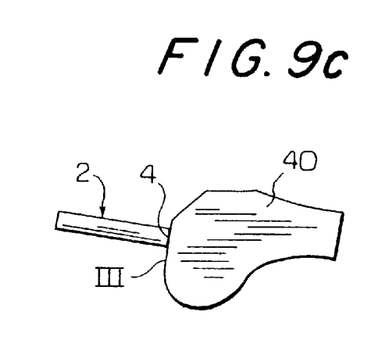

Then the cutting plane II is produced also by way of face milling, which is illustrated in FIG. 9b, with the invention having the setting seen in FIG. 4.

Subsequently, the cutting plane III is produced by face milling, the instrumentation having the setting of FIG. 1.

Figure 9D:
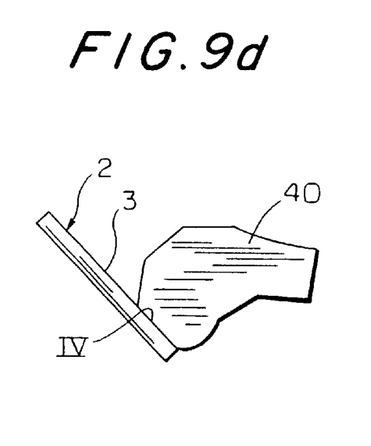
Figure 9E:
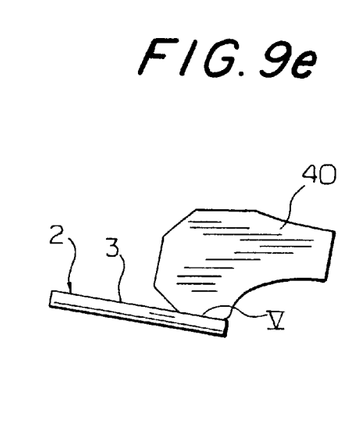

This is followed by a conversion from face milling to cylindrical milling as illustrated in FIG. 6 as compared to FIG. 5. Now the surface area 3 of the milling head 2 is used for milling and moved along the cutting plane IV, i.e. parallel thereto, as seen in FIG. 9d. This is followed by the preparation of the cutting plane V by cylindrical milling which is seen in FIG. 9e.

Figure 9F:
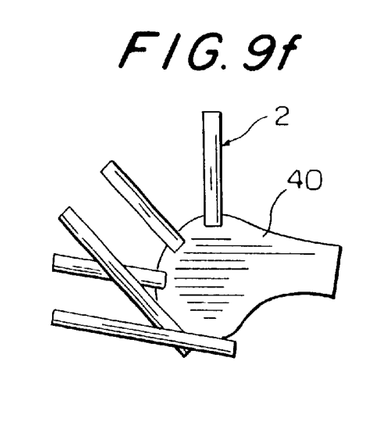

FIG. 9f is a combined illustration of how the individual cutting surfaces I to V are successively produced.

What is claimed is:

1. An instrument for production of fixing surfaces for a knee joint endoprosthesis to be fixed to the femoral condyle that is adjacent to the knee, and to the tibial head, fastening means a rotary milling head comprising (2) which is fixable in relation to the longitudinal axis of the femur (40) and tibia, respectively, by said fastening means and which, in relation to the longitudinal axis, is angularly adjustable in a stable stop position by being pivoted, defining milling planes and which is displaceable in a set milling plane, covering same and working as a face milling cutter or as a cylindrical milling cutter;

wherein the fastening means includes joined-on clamp pieces (27, 28, 29) which are capable of enclasping the respective femur (40); and wherein at least one of a plurality of fastening thorns (30) and holes into which fastening screws are inserted are formed on ends of the joined-on clamp pieces (27, 28, 29).

2. The instrument according to claim 1, wherein a first clamp is capable of gripping over the femur (40) from above, with the clamp (26) having the joined-on clamp pieces (27, 28, 29) which are displaceable one relative to the other and fixable in a stop position.

3. The instrument according to claim 1, wherein the milling head (2) is adjustable in height.

4. The instrument according to claim 1, wherein presetting equipment (17, 18) is provided for setting the position of the axis of a leg.

5. The instrument according to claim 4, wherein a setting equipment for the length of a leg is provided.

6. The instrument according to claim 5, wherein a setting equipment for the size of the prosthesis is provided.

7. The instrument according to claim 6, wherein at least one of different setting equipment and motion of the milling head (2) in the milling planes are driven by a servo motor.

8. The instrument to claim 7, wherein triggering the servo motor is computer-controlled.

9. The instrument according to claim 4, wherein a setting equipment for the length of a leg is provided.

10. The instrument according to claim 5, wherein a setting equipment for the size of the prosthesis is provided.

11. The instrument according to claim 6, wherein at least one of different setting equipment and motion of the milling head (2) in the milling planes are driven by a servo motor.

12. The instrument to claim 7, wherein triggering the servo motor is computer-controlled.

13. An instrument for production of fixing surfaces for a knee joint endoprosthesis to be fixed to the femoral condyle that is adjacent to the knee, and to the tibial head comprising, fastening a rotary milling head (2) which is fixable in relation to the longitudinal axis of the femur (40) and tibia, respectively, by said fastening means and which, in relation to the longitudinal axis, is angularly adjustable in a stable stop position by being pivoted, defining milling planes and which is displaceable in a set milling plane, covering same and working as a face milling cutter or as a cylindrical milling cutter;

wherein a set-screw (31) for a threaded spindle of a stable stop position is provided for height adjustment.

14. The instrument according to claim 2, wherein a first clamp grips over the femur (40) from above, with the clamp (26) having joined-on clamp pieces (27, 28, 29) which are displaceable one relative to the other and fixable in a stop position.

15. The instrument according to claim 13, wherein the milling head (2) is adjustable in height.

16. The instrument according to claim 13, wherein presetting equipment (17, 18) is provided for setting the position of the axis of a leg.

17. An instrument for the production of fixing surfaces for a knee joint endoprosthesis to be fixed to the femoral condyle that is adjacent to the knee, and to tibial head, fastening means a rotary milling head comprising (2) which is fixable in relation to the longitudinal axis of the femur (40) and tibia, respectively, by said fastening means and which, in relation to the longitudinal axis, is angularly adjustable in a stable stop position by being pivoted, defining milling planes and which is displaceable in a set milling plane, covering same and working as a face milling cutter or as a cylindrical milling cutter;

wherein the milling head (2) is linearly translationally displaceable in the milling planes via guide bars (5, 11) and pivotal by a pivot axis (16) or cross support.

18. The instruments according to claim 17, wherein a first clamp grips over the femur (40) from above, with the clamp (26) having joined-on clamp pieces (27, 28, 29) which are displaceable one relative to the other and fixable in a stop position.

19. The instrument according to claim 17, wherein the milling head (2) is adjustable in height.

20. An instrument for production of fixing surfaces for a knee joint endoprosthesis to be fixed to the femoral condyle that is adjacent to the knee, and to the tibial head, comprising fastening means a rotary milling head (2) which is fixable in relation to the longitudinal axis of the femur (40) and tibia, respectively, by said fastening means and which, in relation to this longitudinal axis, is angularly adjustable in a stable stop position by being pivoted, defining milling planes and which is displaceable in a set milling-plane, covering same and working as a face milling cutter or as a cylindrical milling cutter;

wherein infrared markers are provided for navigation.

* * * * *